(12) United States Patent
     Thorn

(10) Patent No.: US 12,564,475 B2
(45) Date of Patent: Mar. 3, 2026

(54) APPARATUS AND SYSTEM FOR CLEANING LENS OF EYE-IMAGING DEVICE AND RELATED METHODS THEREOF

(71) Applicant: PHOENIX-MICRON, INC., Bend, OR (US)

(72) Inventor: Jonathan Roy Thorn, Bend, OR (US)

(73) Assignee: Phoenix-Micron, Inc., Bend, OR (US)

( * ) Notice: Subject to any disclaimer, the term of this patent is extended or adjusted under 35 U.S.C. 154(b) by 102 days.

(21) Appl. No.: 18/665,008

(22) Filed: May 15, 2024

(65) Prior Publication Data

US 2024/0407886 A1      Dec. 12, 2024

Related U.S. Application Data

(60) Provisional application No. 63/471,325, filed on Jun. 6, 2023.

(51) Int. Cl.
    *A61B 90/70*          (2016.01)
    *A61B 3/14*           (2006.01)
    (Continued)

(52) U.S. Cl.
    CPC ................ *A61B 90/70* (2016.02); *A61B 3/14*
    (2013.01); *B08B 3/08* (2013.01); *B08B 7/0014*
    (2013.01)

(58) Field of Classification Search
    CPC .. A61B 90/70; A61B 3/14; B08B 3/08; B08B
                                7/0014; G02B 27/0006
    See application file for complete search history.

(56) References Cited

U.S. PATENT DOCUMENTS

| | | | |
|---|---|---|---|
| 4,953,962 A | 9/1990 | Esswein et al. | |
| 5,154,174 A | 10/1992 | Hawlina | |

(Continued)

FOREIGN PATENT DOCUMENTS

WO          2016205760 A1      12/2016

OTHER PUBLICATIONS

PCT/US2023/076065, "International Preliminary Report on Patentability", Apr. 24, 2025, 8 pages.

(Continued)

*Primary Examiner* — Sharidan Carrillo
(74) *Attorney, Agent, or Firm* — Kilpatrick Townend & Stockton LLP

(57)          ABSTRACT

The present disclosure provides an apparatus that can be attached to a tip portion of an eye-imaging device including the lens. The apparatus includes an annular base having an orifice having a first end and a second end. A contact member may be disposed adjacent the second end of the annular base. The contact member may include a contact surface having a geometry that is configured to fit on a tip of an eye-imaging device. For example, the contact surface may include a tapered region that matches the profile of a tip of an eye-imaging device. The tapered region may provide a frictional fit with a tip of the eye-imaging device such that the contact surface is flush with the surface of the tip. A solution can be deposited in the apparatus and onto a lens surface after it is attached to the tip of the eye-imaging device. In this way, the apparatus prevents any solution from leaking to other areas of the eye-imaging device to clean the lens surface of the eye-imaging device.

6 Claims, 14 Drawing Sheets

```
                    ┌─────────────────────────────────┐
                    │  Provide an eye-imaging device  │
        500         │              510                │
          ↘         └─────────────────────────────────┘
                                    │
                    ┌─────────────────────────────────────────┐
                    │ Provide an apparatus for receiving a     │
                    │           cleaning fluid                 │
                    │              520                         │
                    └─────────────────────────────────────────┘
                                    │
                    ┌─────────────────────────────────────────┐
                    │ Attach the apparatus to the eye-imaging  │
                    │             device                       │
                    │              530                         │
                    └─────────────────────────────────────────┘
                                    │
                    ┌─────────────────────────────────┐
                    │   Fill the apparatus with a fluid│
                    │              540                 │
                    └─────────────────────────────────┘
                                    │
                    ┌─────────────────────────────────────────┐
                    │ Remove the solution from the lens of the │
                    │         eye-imaging apparatus            │
                    │              550                         │
                    └─────────────────────────────────────────┘
```

(51) Int. Cl.
B08B 3/08        (2006.01)
B08B 7/00        (2006.01)

(56)                References Cited

U.S. PATENT DOCUMENTS

| | | | | |
|---|---|---|---|---|
| 5,297,554 | A | 3/1994 | Glynn et al. | |
| 11,752,982 | B2* | 9/2023 | Chen ......................... | B60S 1/52 |
| | | | | 134/18 |
| 2009/0211586 | A1* | 8/2009 | Shea ...................... | A61B 46/10 |
| | | | | 128/849 |
| 2013/0120710 | A1 | 5/2013 | Buckland et al. | |
| 2017/0363849 | A1 | 12/2017 | Doric et al. | |
| 2021/0219905 | A1 | 7/2021 | Hetling et al. | |
| 2022/0304563 | A1* | 9/2022 | Sachs ...................... | B08B 1/165 |
| 2024/0407886 | A1* | 12/2024 | Thorn .................... | A61B 90/70 |
| 2025/0249492 | A1* | 8/2025 | Sonzogni ............... | A46B 13/02 |

OTHER PUBLICATIONS

1 PCT/US2023/076065, "International Search Report and Written Opinion", Jan. 23, 2024, 11 pages.
U.S. Appl. No. 18/377,266, "Non-Final Office Action", Sep. 23, 2025, 9 pages.

* cited by examiner

500

Provide an eye-imaging device
510

Provide an apparatus for receiving a cleaning fluid
520

Attach the apparatus to the eye-imaging device
530

Fill the apparatus with a fluid
540

Remove the solution from the lens of the eye-imaging apparatus
550

APPARATUS AND SYSTEM FOR CLEANING LENS OF EYE-IMAGING DEVICE AND RELATED METHODS THEREOF

CROSS-REFERENCES TO RELATED APPLICATIONS

This application claims priority to U.S. Provisional Patent Application No. 63/471,325, filed Jun. 6, 2023, the disclosure of which is hereby incorporated by reference in its entirety for all intents and purposes.

BACKGROUND OF THE INVENTION

Eye-imaging devices may come in contact with the surface of an open eye during the course of imaging. The lens surface of the eye-imaging device that comes in contact with the eye of a patient may accumulate dirt and debris on the lens surface. For example, during the course of transporting or shipping an eye-imaging device or lens, dirt and debris may accumulate on the lens surface. Given that the camera design of the tip of the eye-imaging device and the shape of the lens, cleaning with tools is difficult without scratching the surface of the lens. Specifically, the lens of the eye-imaging device may be conical so using a tool to remove a film or dirt may damage the lens of the eye-imaging device. Additionally, some cleaning solutions do not sufficiently clean the contact surface of an eye-imaging device due to insufficient soaking or contact with lens of the eye-imaging device. The cleaning solution may drip or fall off the lens during application leading to unwanted exposure to other regions of the eye-imaging device. For example, a polymer solution may require sufficient contact and dwell time on the surface of the lens to transition into polymer. However, in many instances, the polymer solution may drip or fall off the surface lens forming an uneven polymer film. Moreover, the polymer film may be subsequently removed with a sharp tool that can damage the lens of the eye-imaging device.

Therefore, systems and methods are needed for efficient ways to clean a lens surface of an eye-imaging device without damaging the surface of the lens and providing sufficient time for a cleaning solution to contact the lens surface to remove dirt or debris.

BRIEF SUMMARY OF THE INVENTION

The present disclosure relates to an apparatus, system, and method for cleaning the lens of an eye-imaging device. In particular, the present disclosure provides an apparatus, system, and method for cleaning the lens of an eye-imaging device that can significantly reduce costs, improve efficiency, prevent damage to a lens surface, and maintain optical clarity.

Embodiments of the present disclosure include an apparatus for cleaning a lens of an eye-imaging camera. The apparatus includes; an annular base comprising an orifice, the annular base comprising a first end and a second end; a contact member disposed adjacent to the second end of the annular base, wherein the contact member has a diameter less than the annular base such that the contact member fits within the annular base, wherein the contact member includes a contact surface; and a top region disposed at the first end of the annular base, the top region comprising a lip extending outwardly away from the annular base; wherein the contact surface includes a first contact end and a second contact end, wherein the contact surface tapers from the first contact end to the second contact end. In some embodiments, the annular base comprises a sidewall that is substantially parallel with a long axis of the apparatus. In some embodiments, the annular base decreases in diameter from the first end to the second end. In some embodiments, the contact member is removably attached to the annular base. In some embodiments, the contact member is integral with the annular base. In some embodiments, the contact surface further comprises an adhesive. In some embodiments, the annular base comprises one or more tangs attached to an outer surface of the annular base.

Embodiments of the present disclosure include a system for cleaning a lens of an eye-imaging device, the system comprising: an eye-imaging device comprising a tip including a lens; an apparatus configured to attach to the tip of the eye-imaging device, wherein the apparatus comprises: an annular base comprising an orifice, the annular base comprising a first end and a second end; a contact member disposed adjacent to the second end of the annular base, wherein the contact member has a diameter less than the annular base such that the contact member fits within the annular base, wherein the contact member includes a contact surface; and a top region disposed at the first end of the annular base, the top region comprising a lip extending outwardly away from the annular base; wherein the contact surface includes a first contact end and a second contact end, wherein the contact surface tapers from the first contact end to the second contact end; and a cleaning solution. In some embodiments, the cleaning solution comprises a polymer solution comprising a solvent and a polymer. In some embodiments, the apparatus is configured to be press fit onto the tip of the eye-imaging device. In some embodiments, the contact surface of the contact member is configured to seal the apparatus to the tip of the eye-imaging device. In some embodiments, an interior volume of the apparatus is configured to receive the cleaning solution. In some embodiments, the contact surface corresponds to a profile of the tip of the eye-imaging device. In some embodiments, the apparatus is press fit onto the tip of the eye-imaging device, wherein the contact member is below the lens and the top region is above the lens.

Embodiments of the present disclosure include a method of cleaning a lens of an eye-imaging device, the method comprising: providing an eye-imaging device comprising a tip including a lens; providing an apparatus for receiving a cleaning solution, wherein the apparatus comprises: an annular base comprising an orifice, the annular base comprising a first end and a second end; a contact member disposed adjacent to the second end of the annular base, wherein the contact member has a diameter less than the annular base such that the contact member fits within the annular base, wherein the contact member includes a contact surface; and a top region disposed at the first end of the annular base, the top region comprising a lip extending outwardly away from the annular base; wherein the contact surface includes a first contact end and a second contact end, wherein the contact surface tapers from the first contact end to the second contact end; and attaching the apparatus to the tip of the eye-imaging device; filling the apparatus with the cleaning solution; and removing the cleaning solution from the lens of the eye-imaging device. In some embodiments, attaching the apparatus to the eye-imaging device comprises press fitting the apparatus to the eye-imaging device such that the contact surface of the contact member is flush with the tip of the eye-imaging device. In some embodiments, removing the cleaning solution comprises removing the apparatus from the eye-imaging device to remove the cleaning solution from a surface of the lens. In some embodiments, the cleaning solution comprises a polymer solution comprising a solvent and a polymer. In some embodiments, the method further comprises contacting the polymer solution with the lens for a sufficient period of time for the solvent to dry to form a polymer film. In some embodiments, the method further comprises sealing the top region of the apparatus.

Numerous benefits are achieved by way of the present disclosure over conventional techniques. For example, embodiments of the present disclosure provide an apparatus that can be attached to an eye-imaging device that can retain cleaning solutions (e.g., polymer solution). The apparatus is configured to attach to a tip of an imaging camera to receive a cleaning solution on a lens surface at the tip of the imaging camera. The apparatus can include annular base including a contact surface that conforms to and seals the tip of an eye-imaging device. In this way, a cleaning solution can be deposited in the apparatus such that it remains in contact with a lens surface of the eye-imaging device. The apparatus can be removed from the eye-imaging device after each use to prevent cross contamination. As explained in this disclosure, the apparatus described herein prevents dripping of solutions during cleaning and allows sufficient dwell time for the cleaning solution and the lens of the eye-imaging device. These and other embodiments of the disclosure, along with many of their advantages and features, are described in more detail in conjunction with the text below and attached figures.

DETAILED DESCRIPTION OF THE INVENTION

Figure 1:
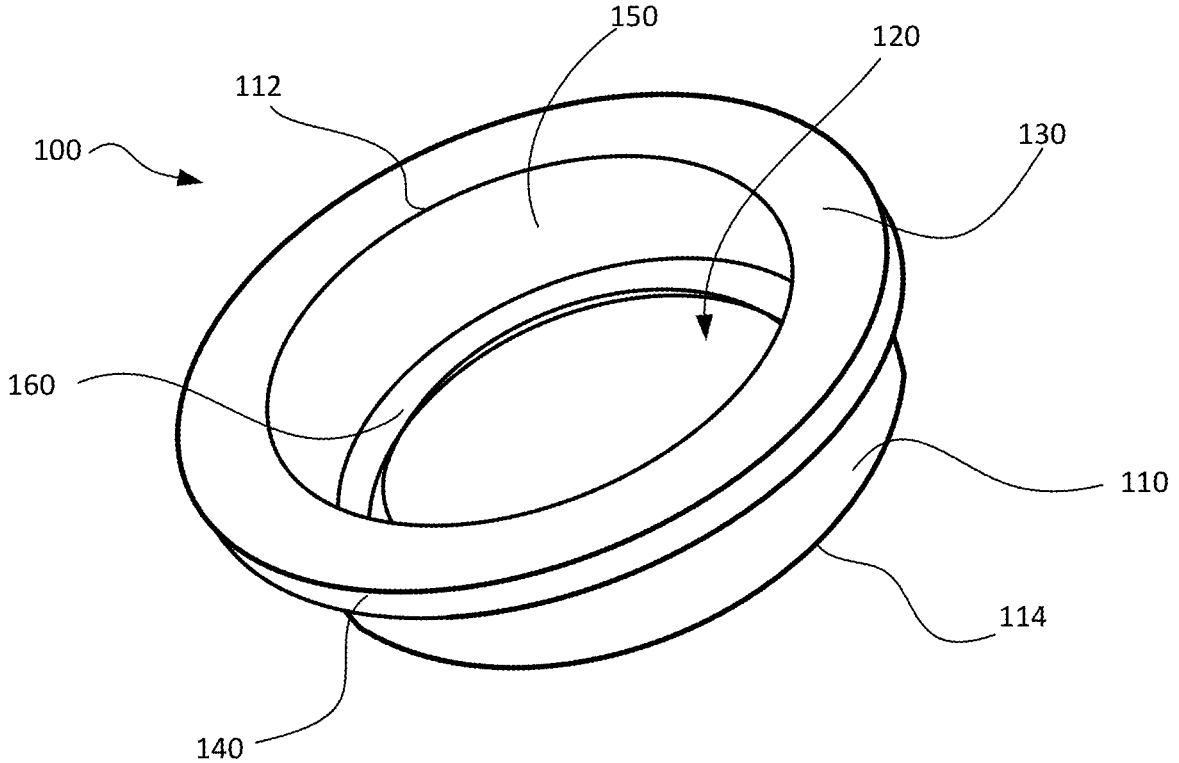
FIG. 1 illustrates a top perspective view of an apparatus according to some embodiments.

The present disclosure describes a number of embodiments related to an apparatus, system, and method for cleaning a lens surface of an eye-imaging device. In some embodiments, the present disclosure provides an apparatus that can be attached to a tip portion of an eye-imaging device including a lens. The lens may include a convex lens surface. The apparatus includes an annular base having an orifice having a first end and a second end. A contact member may be disposed adjacent the second end of the annular base. The contact member may include a contact surface having a geometry that is configured to fit on a tip of an eye-imaging device. For example, the contact surface may include a tapered region that matches the profile of a tip of an eye-imaging device. The tapered region may provide a frictional fit (or press fit) with a tip of the eye-imaging device such that the contact surface is flush with the surface of the tip. A solution can be deposited in the interior volume of the apparatus after it is attached to the tip of the eye-imaging device. For example, the solution can be deposited on a lens surface at the tip of the eye-imaging device. In this way, the apparatus prevents any solution from leaking to other areas of the eye-imaging device to clean the lens surface of the eye-imaging device.

In conventional processes, the lens surface of an eye-imaging device is cleaned by applying a solution directly to the lens of the eye-imaging device. For example, a polymer solution can be deposited on the lens surface of the eye-imaging device. However, the polymer solution may fall off the lens causing spillage. Additionally, the polymer solution may not contact the surface of the lens for a sufficient period of time to transition into a polymer for removing contaminants from the surface of the lens. As a result, the lens of the eye-imaging device is not sufficiently cleaned and the polymer solution may leak to unwanted regions of the eye-imaging device. In some embodiments, the polymer solution may transition to a polymer film that may be removed with a sharp tool to separate the film from the surface of the lens. However, the lens be scratched during this process and result in a defective lens.

As described above, the apparatus described herein can be removably attached to an eye-imaging device to retain a cleaning solution (e.g., polymer solution). In some embodiments, the apparatus is configured to enclose a portion of the tip of an eye-imaging device. The apparatus provides an interior volume that can receive a cleaning solution to clean the lens of an imaging device. In some embodiments, the apparatus is substantially annular and can include a contact member that is tailored to a specific profile of a tip of an eye-imaging device. In some embodiments, the annular base may include a plurality of barbs for good bonding with, for example, a polymer solution. The apparatus described herein avoids leakage that may damage the imaging device. The apparatus described herein can be a disposable apparatus that can be removed from the imaging device after each use thereby avoiding cross-contamination. The apparatus described herein provides an improved fit to the imaging device that prevents the apparatus from slipping or sliding on the tip of an imaging device during cleaning. Additionally, the apparatus can be removed from the tip of an imaging device along any formed polymer films thereby avoiding the use of any tools to remove the polymer film that may damage the lens.

FIG. 1 illustrates a top perspective view of an apparatus for cleaning a lens of an eye-imaging device according to some embodiments. The apparatus 100 comprises an annular base 110 including an orifice 120. The annular base 110 includes a first end 112 and a second end 114. In some embodiments, the annular base 110 may have a constant diameter from the first end 112 to the second end 114. In some embodiments, the annular base 110 includes a sidewall 150 that decreases in diameter (e.g., tapers) from the first end 112 to the second end 114. In this embodiment, the diameter of the annular base 110 varies from the first end 112 to the second end 114. For example, the annular base 110 decreases in diameter from the first end 112 to the second end 114 providing a funnel for a cleaning solution.

The orifice 120 of the annular base 110 is configured to receive a tip of an imaging device including a lens. As shown in FIG. 1, the annular base 110 is ring-shaped to provide an orifice 120 that corresponds to the shape of a conical tip of an imaging device including the lens. In some embodiments, the shape of the annular base 110 can be modified to match the shape of the tip of an imaging device. For example, the annular base 110 can be oval-shaped to correspond to an oval-shaped tip or lens of an imaging device. The annular base 110 is configured to be removably attached to a tip of an imaging device. In some embodiments, the annular base 110 is attached to tip of an imaging device by a frictional press fit. For example, annular base 110 can be press fit to a tip of an imaging device such that a portion of the annular base 110 rests below the lens.

The apparatus 100 includes a top region 130. The top region 130 is disposed at a distal end of the annular base 110. The top region 130 includes a lip 140. The lip 140 extends outwardly from the top region 130. For example, the lip 140 can surround the circumferential edge of the top region 130 of the annular base 110. The lip 140 has a larger circumference than the annular base 110. In this way, the lip 140 can be used as a surface to apply force to attach the apparatus 100 to the tip of an imaging device. In some embodiments, the lip 140 can be perpendicular to a long axis of the apparatus 100. In some embodiment, the lip 140 can be disposed at an acute angle to a long axis of the apparatus 100. The lip 140 can assist with retaining fluid (e.g., cleaning solution) within the annular base 110.

Figure 2:
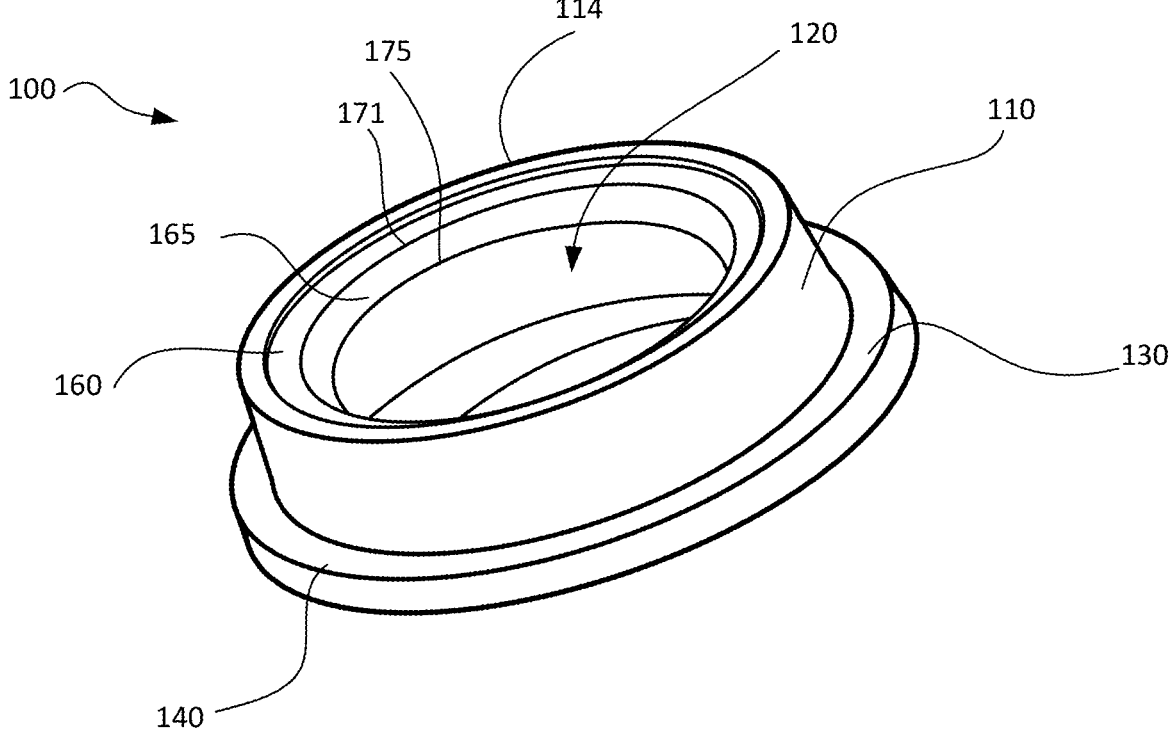
FIG. 2 illustrates a bottom perspective view of an apparatus according to some embodiments.
Figure 3:
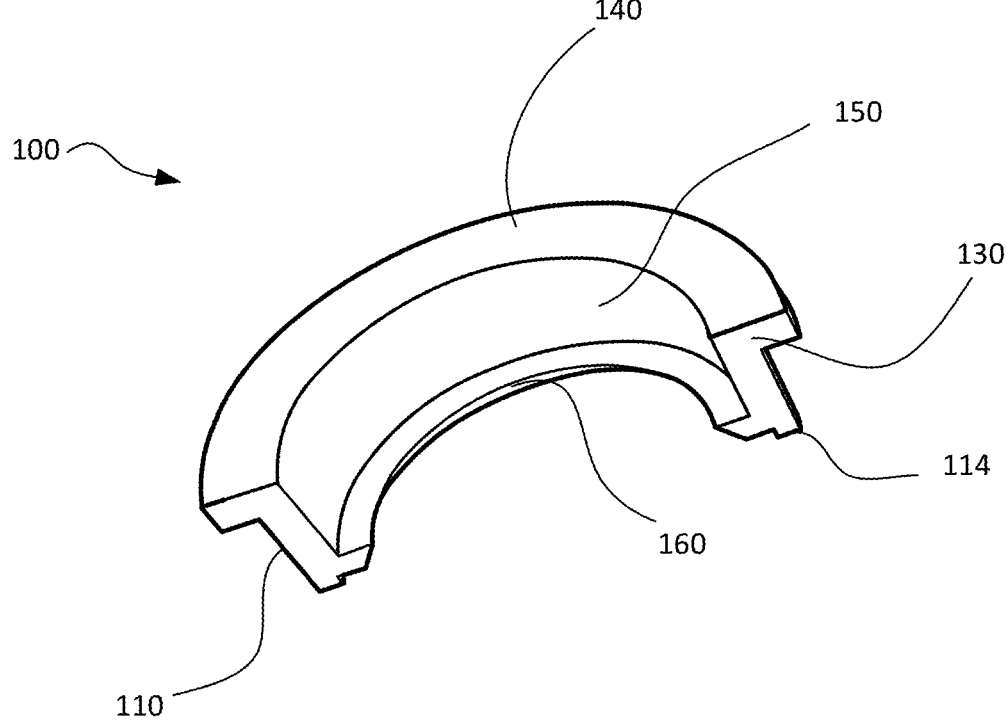
FIG. 3 illustrates a cutaway view the apparatus along a horizontal plane according to some embodiments.

FIG. 2 illustrates a bottom perspective view of the apparatus 100 of FIG. 1. The annular base 110 includes a contact member 160 that is configured to contact a portion of the tip of an imaging device. The contact member 160 is disposed at a region adjacent the second end 114 of the annular base 110. In some embodiments, the contact member 160 is annular. For example, the contact member 160 can have a shape the corresponds to the shape of the annular base 110. The diameter of the contact member 160 is less than the diameter of the annular base 110. The outer surface of the contact member 160 contacts the inner surface of the annular base 110. For example, FIG. 3 shows that the annular base 110 includes a contact member 160 abutting the sidewall 150 of the annular member. The sidewall 150 may be substantially parallel to the long axis of the apparatus 100. In some embodiments, the sidewall 150 forms an obtuse angle with the contact member 160. For example, the sidewall 150 may taper from the first end 112 to the second end 114 of the annular base 110.

FIG. 2 shows that the contact member 160 within the annular base 110. The contact member 160 includes a contact surface 165. The contact surface 165 is configured to contact the surface of a conical tip of an imaging device. The contact surface 165 may have a tapered profile to match or correspond to the profile of a contact tip. For example, the contact surface 165 may taper from a first contact end 171 to a second contact end 175 such the contact surface 160 has a smaller diameter at the first contact end 171 than the second contact end 175, or vice versa. In some embodiments, the contact surface 165 may match the profile of the outer surface of the tip of an imaging device for a frictional fit. The contact surface 165 of the contact member 160 is configured to seal the apparatus 100 to the tip of an imaging device. The contact surface 165 seals the region between the tip of the imaging device and the lens such that one end of the orifice 120 is completely enclosed. The contact surface 165 may include a plurality of barbs (not shown) to promote adhesion with a cleaning solution (e.g., a polymer solution).

In some embodiments, the contact member 160 is a removable element from the apparatus 100. In instances that the contact member 160 is removable, a plurality of contact members 160 including contact surfaces 165 having different profiles can be provided to correspond to the profile and shape of a tip of an imaging device. In some embodiments, the contact member 160 can be formed integrally with the annular member. In some embodiments, when the apparatus 100 is attached to the tip of an imaging device, the contact member 160 is below the lens of the imaging device and the top region 130 is above the lens of the imaging device.

In some embodiments, the annular base 110 and/or contact member 160 may include a fastening member that is configured to mate with a fastening member on the tip of an imaging device. For example, the tip of an imaging device may include a groove on an outer surface and the annular base 110 or contact member 160 may include a protrusion on an inner surface. The protrusion on the inner surface of the annular base 110 or contact member 160 may fit within the groove on the outer surface of the tip to attach the components. In some embodiments, the annular base 110 may include one or more tangs (not shown) on an outer surface. The tangs may be configured to attach the annular base 110 onto a substrate. For example, a force can be applied to the tangs to press fit the annular base 110 onto an imaging device such that the contact surface 165 of the contact member 160 is flush with the tip of the imaging device.

FIGS. 4A-4E illustrate multiple views of a system for cleaning an imaging device. The system includes the apparatus 100 of FIGS. 1-3 for receiving a cleaning solution therein and an imaging device 200. The imaging device 200 includes a tip 210 including a lens 220. The apparatus 100 is configured to be attached to the imaging device 200. In some embodiments, the apparatus 100 and a cleaning solution (e.g., polymer solution comprising a polymer dissolved in a solvent) can be provided in a kit to clean the lens surface of an imaging device. As described herein, the apparatus 100 can be press fit onto the tip 210 of the imaging device 200. For example, a force can be applied to the lip 140 of the apparatus 100 to attach the apparatus to the tip 210 of the imaging device 200.

Figure 4A:
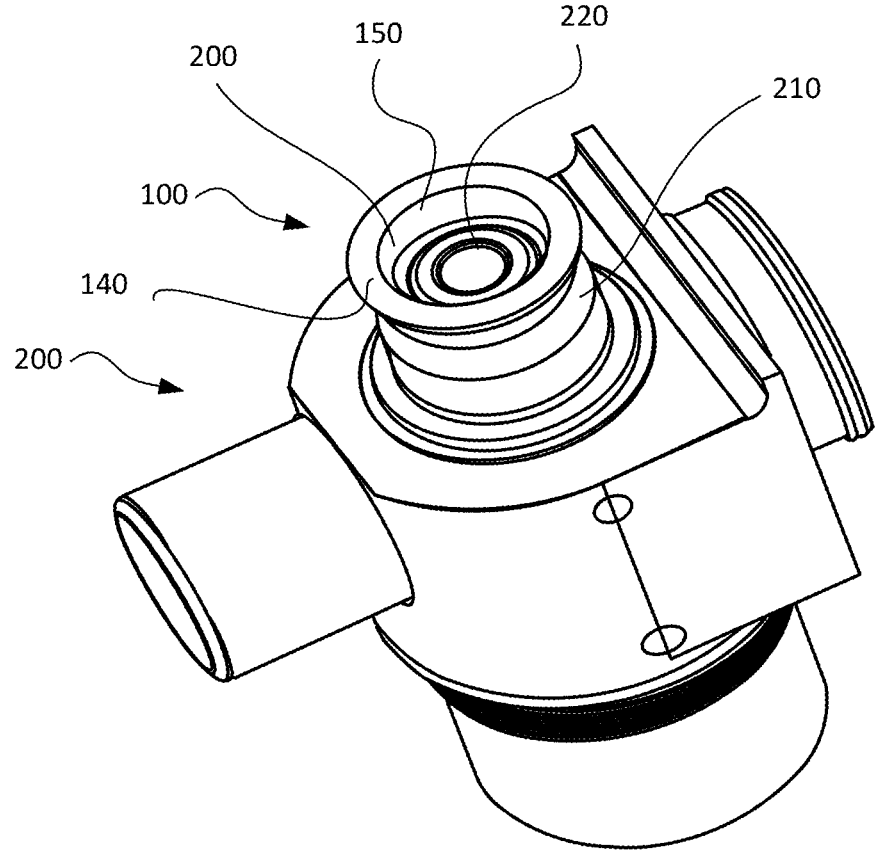
FIG. 4A illustrates a front perspective view of a system including an apparatus attached to an eye-imaging device according to some embodiments.
Figure 4B:
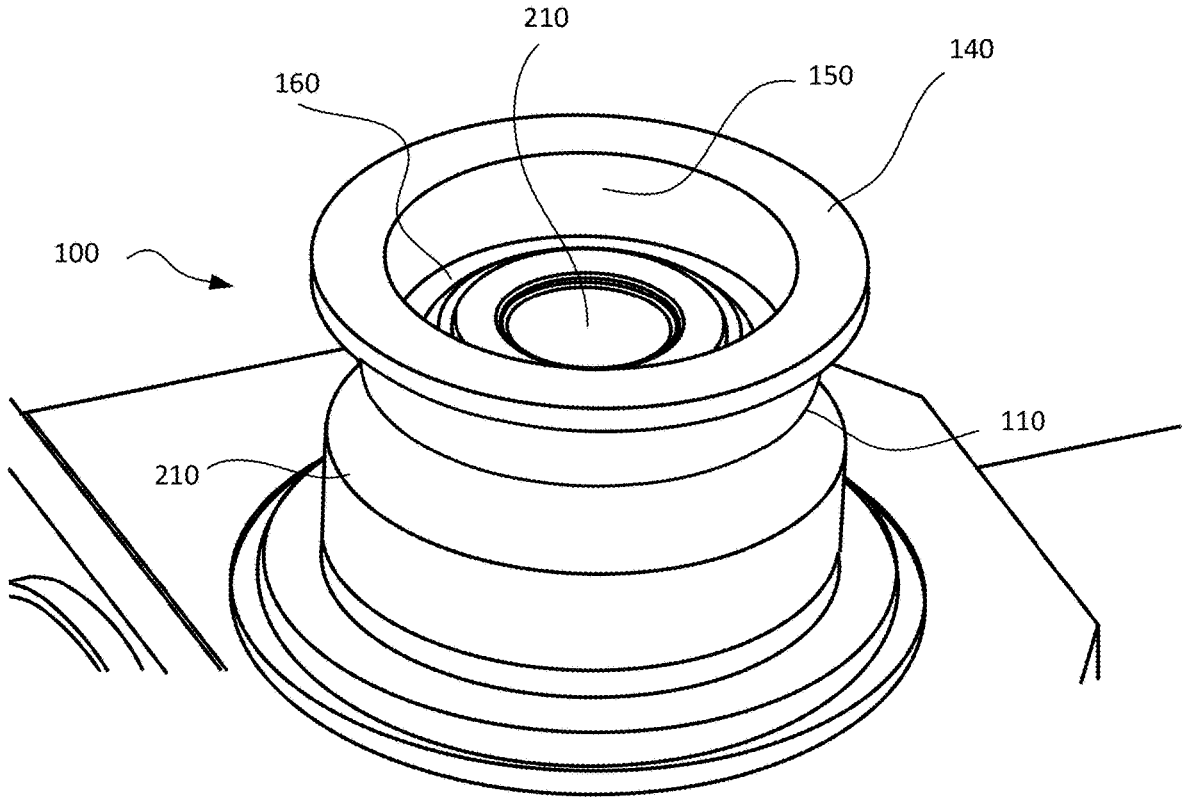
FIG. 4B illustrates a closeup view of the system including an apparatus attached to an eye-imaging device according to some embodiments.

FIG. 4A shows the apparatus 100 attached to the tip 210 of the imaging device 200 and FIG. 4B shows a close-up view of the image of FIG. 4A. The apparatus 100 seals the lens 220 at the tip 210 of the imaging device 200 from the other components of the imaging device 200. The sidewall 150 of the annular base defines the interior volume for retaining a cleaning solution therein. For example, a cleaning solution can be deposited into the interior volume of the apparatus 100. The cleaning solution is bound by the sidewall 150 of the annular base and the contact member 160 to retain the cleaning solution therein. The lip 140 forms the top portion of the apparatus 100. The height of the sidewall 150 from the contact member 160 to the lip 140 is the maximum height for receiving cleaning solution without leakage onto other parts of the imaging device 200. In some embodiments, the top region 130 of the apparatus 100 can be sealed. For example, a film or cover can be placed over the top region 130 of the apparatus 100 to prevent leakage.

Figure 4C:
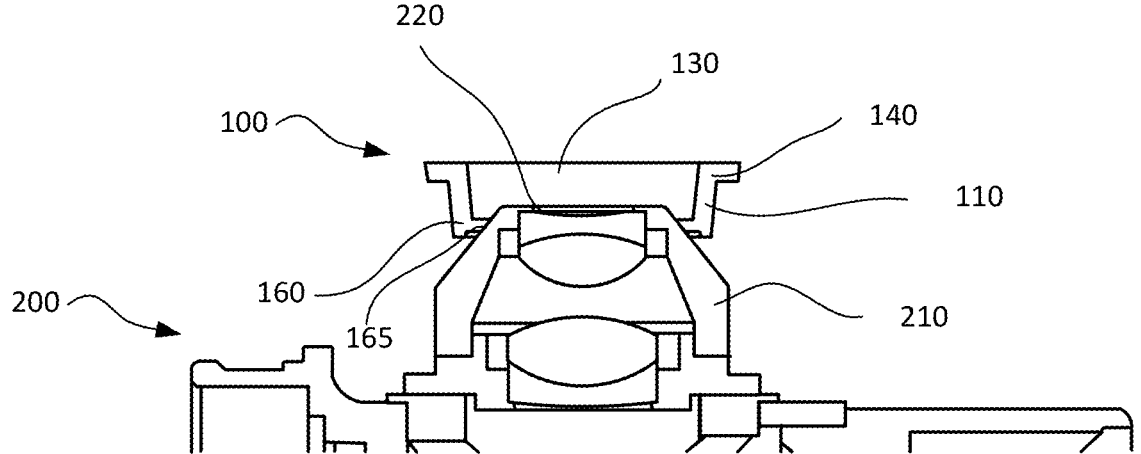
FIG. 4C illustrates a side cutaway view of the system including an apparatus attached to an eye-imaging device according to some embodiments.
Figure 4D:
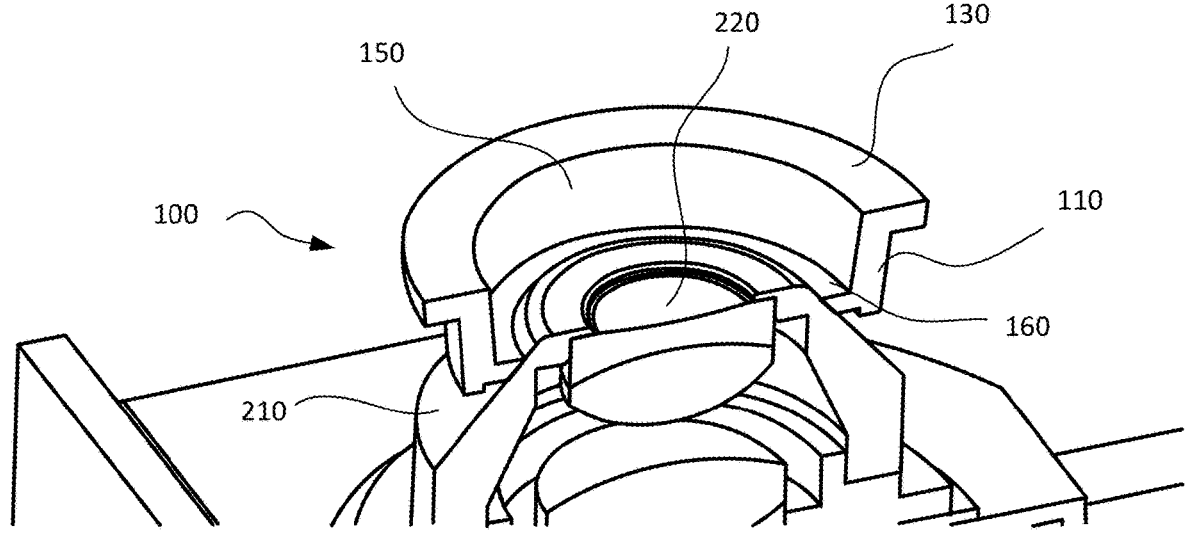
FIG. 4D illustrates a top-side cutaway view of the system including an apparatus attached to an eye-imaging device according to some embodiments.
Figure 4E:
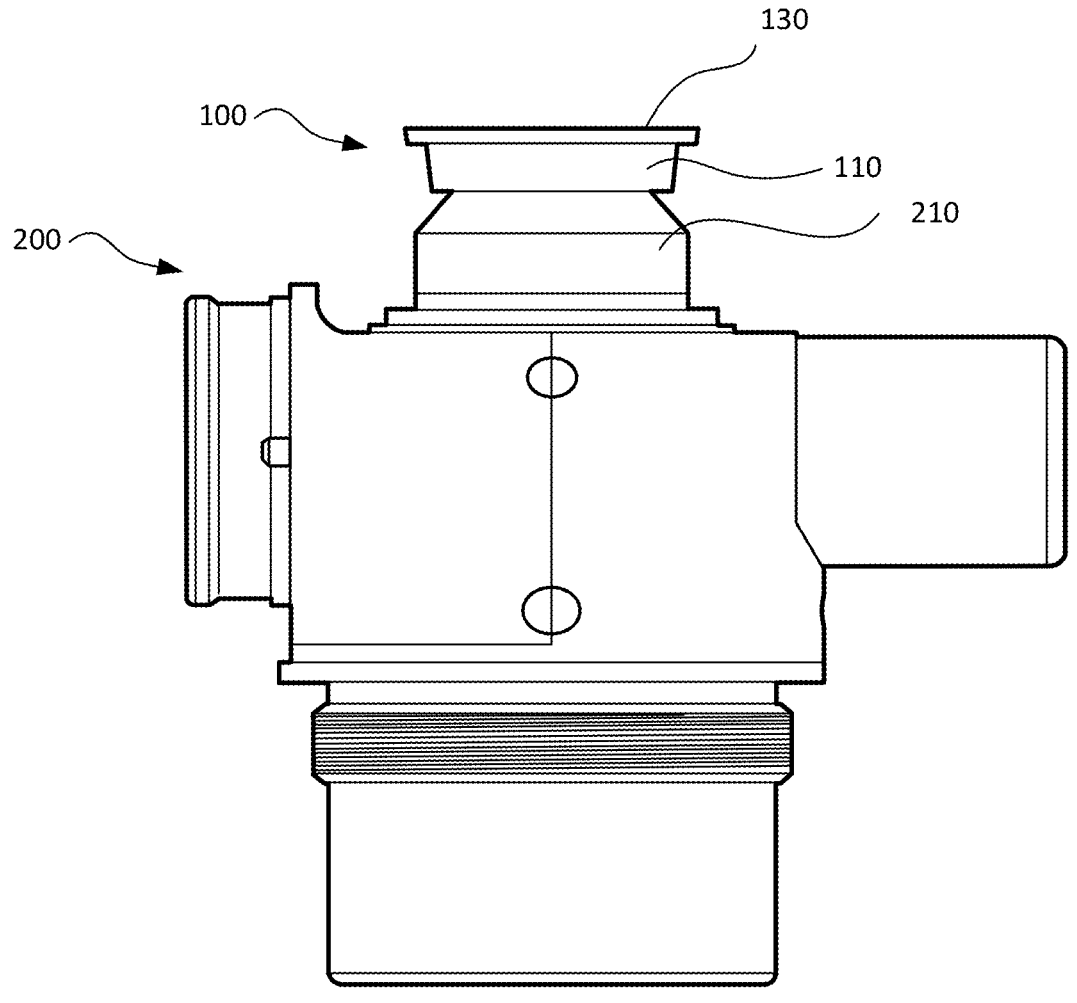
FIG. 4E illustrates a side perspective view of the system including an apparatus attached to an eye-imaging device according to some embodiments.

FIGS. 4C and 4D show cutaway views of the apparatus 100 attached to the tip 210 of the imaging device 200. As shown in FIGS. 4C and 4D, the contact member 160 of the annular base 110 directly contacts the tip 210 of the imaging device 200. In particular, the contact surface 165 of the contact member 160 is flush with the surface of the tip 210 of the imaging device 200. The contact surface 165 provides a seal between the apparatus 100 and the tip 210 of the imaging device 200. For example, FIG. 4E shows that the tip 210 of the imaging device 200 is sealed from remaining parts of the imaging device 200. In this way, a cleaning solution can be received within the interior volume of the apparatus 100 without leakage. A portion of the annular base 110 including the contact member 160 is positioned below the lens 220 of the imaging device 200 and the top region 130 including the lip 140 is positioned above the lens 220. Once the apparatus 100 is attached to the tip 210 of imaging device 200, the apparatus 100 provides an interior volume for receiving a cleaning solution.

Figure 5:
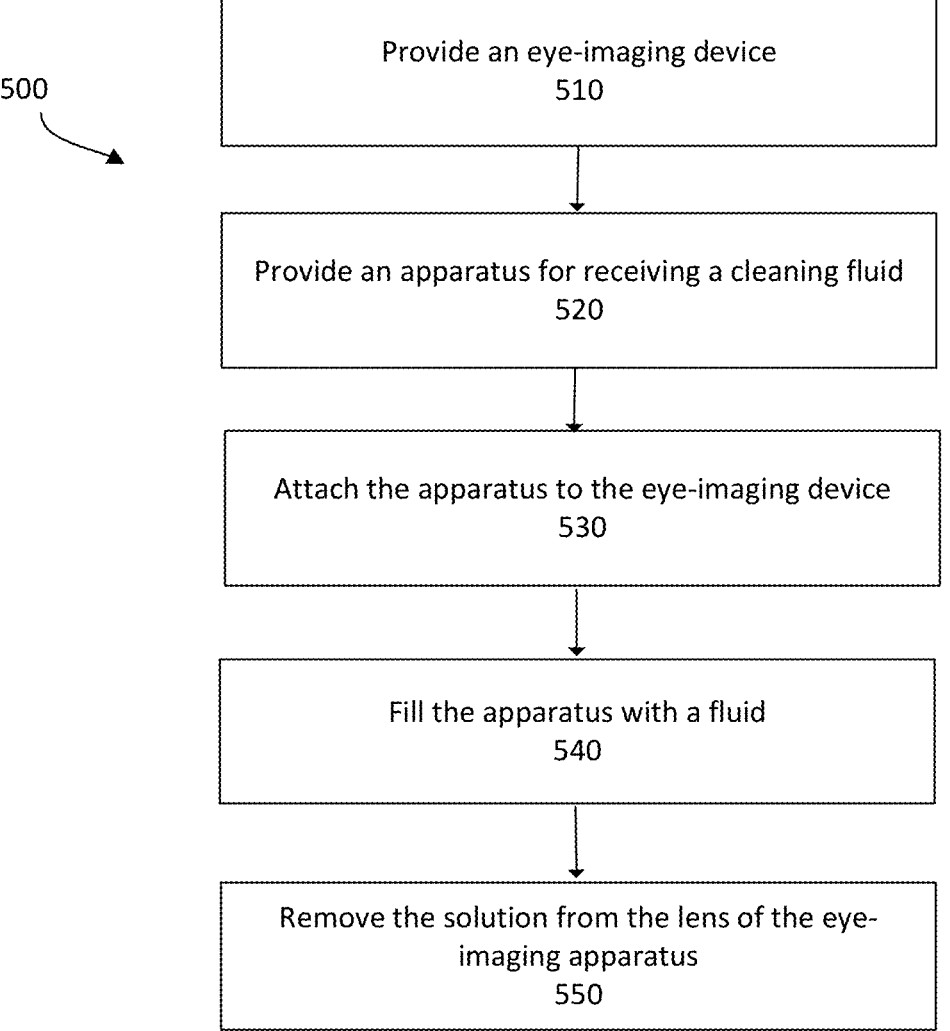
FIG. 5 provides a flow diagram of a method of cleaning a lens of an eye-imaging device according to some embodiments.

FIG. 5 provides a flow diagram of a method of cleaning an eye-imaging device according to some embodiments. The method 500 may include providing an eye-imaging device 510. The eye-imaging device may include a tip including a lens. In some embodiments, the eye-imaging device can be any imaging device that includes one or more lenses and other optical elements. In some embodiments, the eye-imaging device may include a field adjustable optics lens as described in U.S. Provisional Application No. 63/146,330, which is incorporated by reference in its entirety for all intents and purposes.

The method 500 may include providing an apparatus 520 for receiving a cleaning solution. The apparatus may be the apparatus described herein in FIGS. 1-4E. In some embodiments, the apparatus may be provided in a kit including a cleaning solution. For example, the kit may be a disposable package including the apparatus having a contact member that matches the profile of the tip of an eye-imaging device, a cleaning solution disposed in a package with a seal, and an alcohol patch. The cleaning solution can be a polymer solution that is received by the apparatus. In some embodiments, the polymer solution may comprise a polymer dissolved in a solvent. The apparatus may include an annular base having an orifice having a first end and a second end. A contact member may be disposed adjacent the second end of the annular base. The contact member may include a contact surface having a geometry that is configured to fit on a tip of an eye-imaging device. For example, the contact surface may include a tapered region that matches the profile of a tip of an eye-imaging device. The tapered region may provide a frictional fit with a tip of the eye-imaging device such that the contact surface is flush with the surface of the tip. A solution can be deposited in the apparatus after it is attached to the tip of the eye-imaging device. In this way, the apparatus prevents any solution from leaking to other areas of the eye-imaging device to clean the lens surface of the eye-imaging device.

The method 500 may include attaching the apparatus to the eye-imaging device 530. For example, the apparatus may be press fit onto the tip of the eye-imaging device. To attach the apparatus to the eye-imaging device, a force may be exerted on a lip portion of the apparatus to attach the annular base to the tip of the eye-imaging device. For example, a force is exerted on the apparatus until the contact surface of the contact member is flush with the tip of eye-imaging device. In some embodiments, the contact surface may include an adhesive for securing the apparatus on the eye-imaging device. In some embodiments, the annular base may include a plurality of tangs. A force may be exerted on the plurality of tangs to attach the annular base to the tip of the imaging device.

The method 500 includes filling the apparatus with a fluid 540. In some embodiments, the fluid is a cleaning solution. For example, the cleaning solution is a polymer solution composition. In some embodiments, the polymer solution may comprise a polymer dissolved in a solvent. The polymer solution can be deposited on the lens surface as liquid. After the solvent dries, the polymer forms a solid film on the surface of the lens. The polymer solution can be poured into the apparatus to a sufficient depth such that the polymer solution covers the lens of the eye-imaging device. The polymer solution can remain on the lens until the solvent dries and a polymer film is formed. Specifically, the polymer solution contacts the lens for a sufficient period of time to form a polymer film. In some embodiments, the solvent of the polymer solution dissolves biological substances. For example, fingerprints can dissolve in the solvent and chemical bond to the polymer film. Additionally, although dirt and debris do not dissolve, the dirt and debris are encased in the polymer film for effective removal.

The method 500 includes removing the solution from the eye-imaging device 550. In some embodiments, after the polymer solution has solidified, the polymer solution and/or apparatus can be removed from the lens to provide a clean surface. For example, if the polymer solution solidifies and adheres to portions of the apparatus, the apparatus can be removed to peel the polymer film from the lens of the eye-imaging device.

It should be appreciated that the specific steps illustrated in FIG. 5 provide a particular method of attaching an apparatus to an eye-imaging device according to some embodiments. Other sequences of steps may also be performed according to alternative embodiments. For example, alternative embodiments of the present invention may perform the steps outlined above in a different order. Moreover, the individual steps illustrated in FIG. 5 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 6:
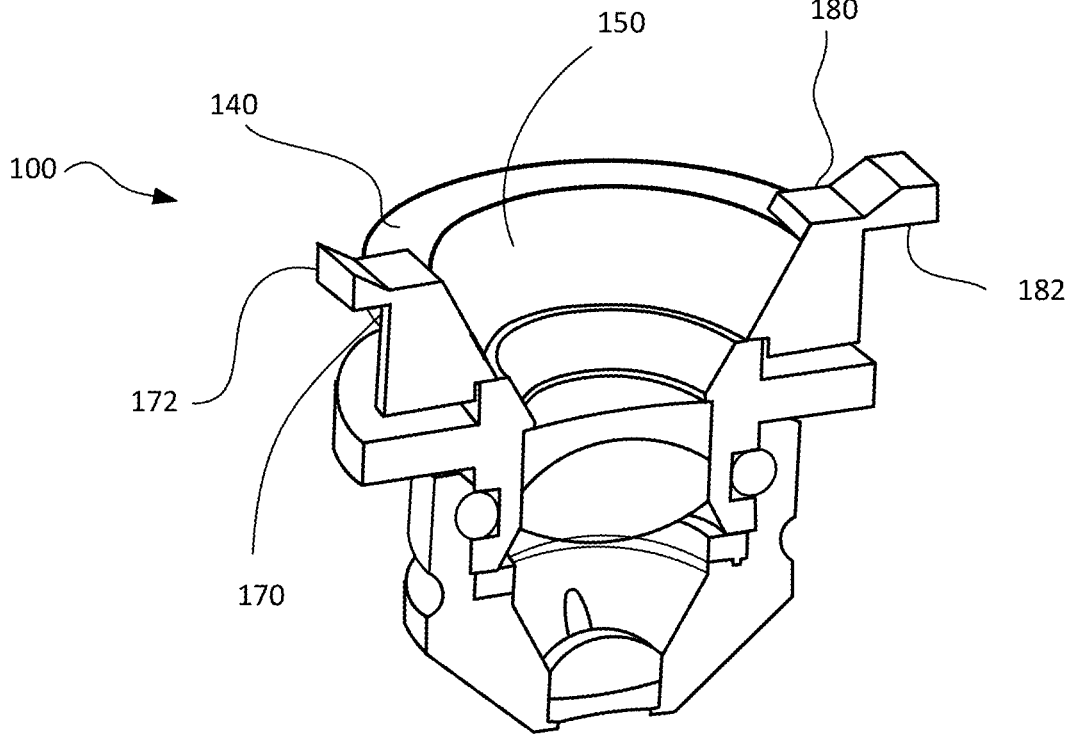
FIG. 6 illustrates another embodiment of the apparatus attached to an eye-imaging device according to some embodiments.

FIG. 6 illustrates another embodiment of the apparatus attached to an eye-imaging device according to some embodiments. The apparatus 100 includes a first leg 170 and a second leg. The first leg 170 and the second leg 180 are disposed on the lip 140 of the apparatus. In some embodiments, the first leg 170 and the second leg 180 are tabs that extend outwardly from the lip 140. For example, the first leg 170 and the second leg 180 may include raised portions 172, 182 that extends outwardly past the circumference of the lip 140. The raised portions 172, 182 may be configured to be grasped by a user to place or remove the apparatus 100. In some embodiments, the length or height of the first leg 170 and the second leg 180 may be different. For example, the first leg 170 may have a greater than the second leg 180. The length of the second leg 180 can facilitate gripping the raised portion 182. In some embodiments, the first leg 170 may have a length that extends to the outer circumference of the lip 140.

In some embodiments, a polymer solution can be deposited into the apparatus 100. The polymer solution may comprise a solvent and a polymer. The solvent can be an organic solvent. In some embodiments, the solvent can be a fast evaporating solvent (e.g., less than 5 minutes). After the polymer solution transitions to a polymer film, the apparatus 100 can be removed from the eye-imaging device to peel the polymer film from the surface of the lens. For example, a user can grasp one or both of the first leg 170 and the second leg 180 to remove the polymer film along with the apparatus from the lens of the eye-imaging device.

Figure 7A:
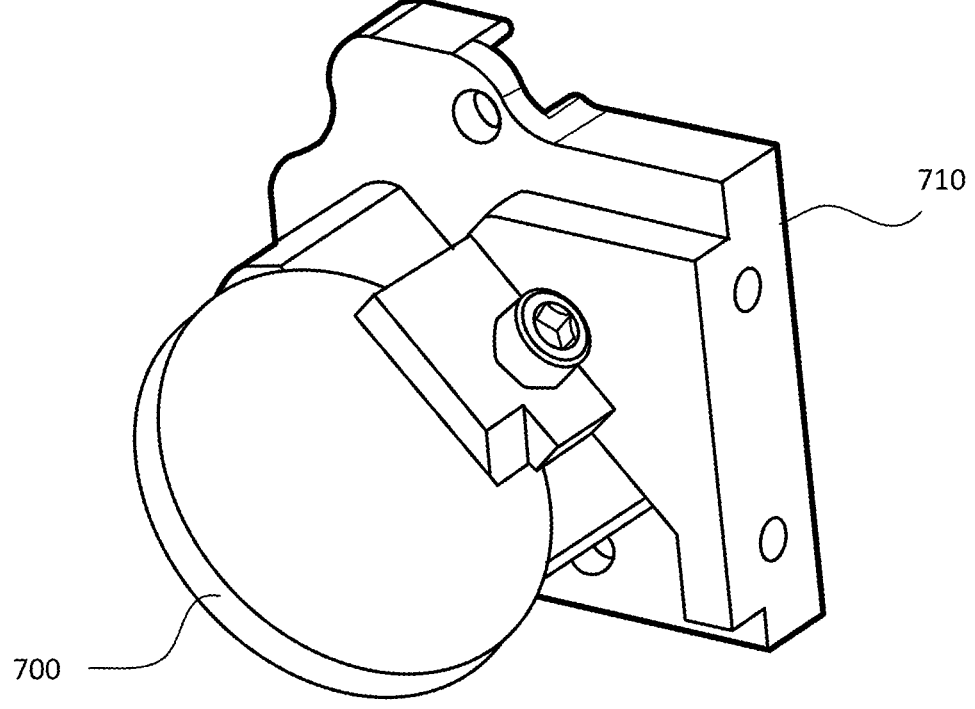
FIGS. 7A-7D illustrates illustrate a process of cleaning a lens using the apparatus of FIG. 6 according to some embodiments.

FIGS. 7A-7D illustrates illustrate a process of cleaning a lens using the apparatus of FIG. 6 according to some embodiments. FIG. 7A shows a flat optic 700 is secured in a clamping device 710. The clamping device 710 may include screws that provides a clamping force to hold the flat optic 700 in place. For example, the screws can be tightened to increase the clamping force on the flat optics 700. The clamping device 710 can hold an edge of the flat optic 700 to expose a majority (e.g., greater than 80%) of the flat optic 700 surface for cleaning. Although the application discusses cleaning a lens surface at the conical tip of an imaging device, the apparatus described herein can be used to clean any lens or optics surface. For example, FIGS. 7A and 7B the apparatus described herein used to clean a lens that is detached from an imaging device. As such, the apparatus described herein can be used to clean any lens surface.

Figure 7B:
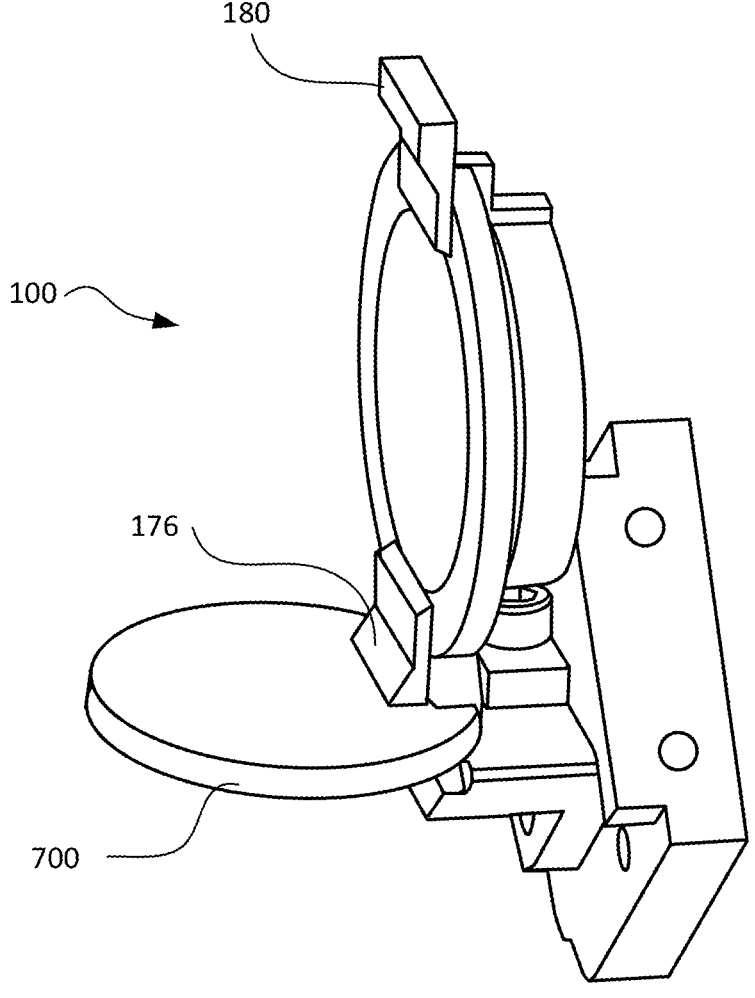
Figure 7C:
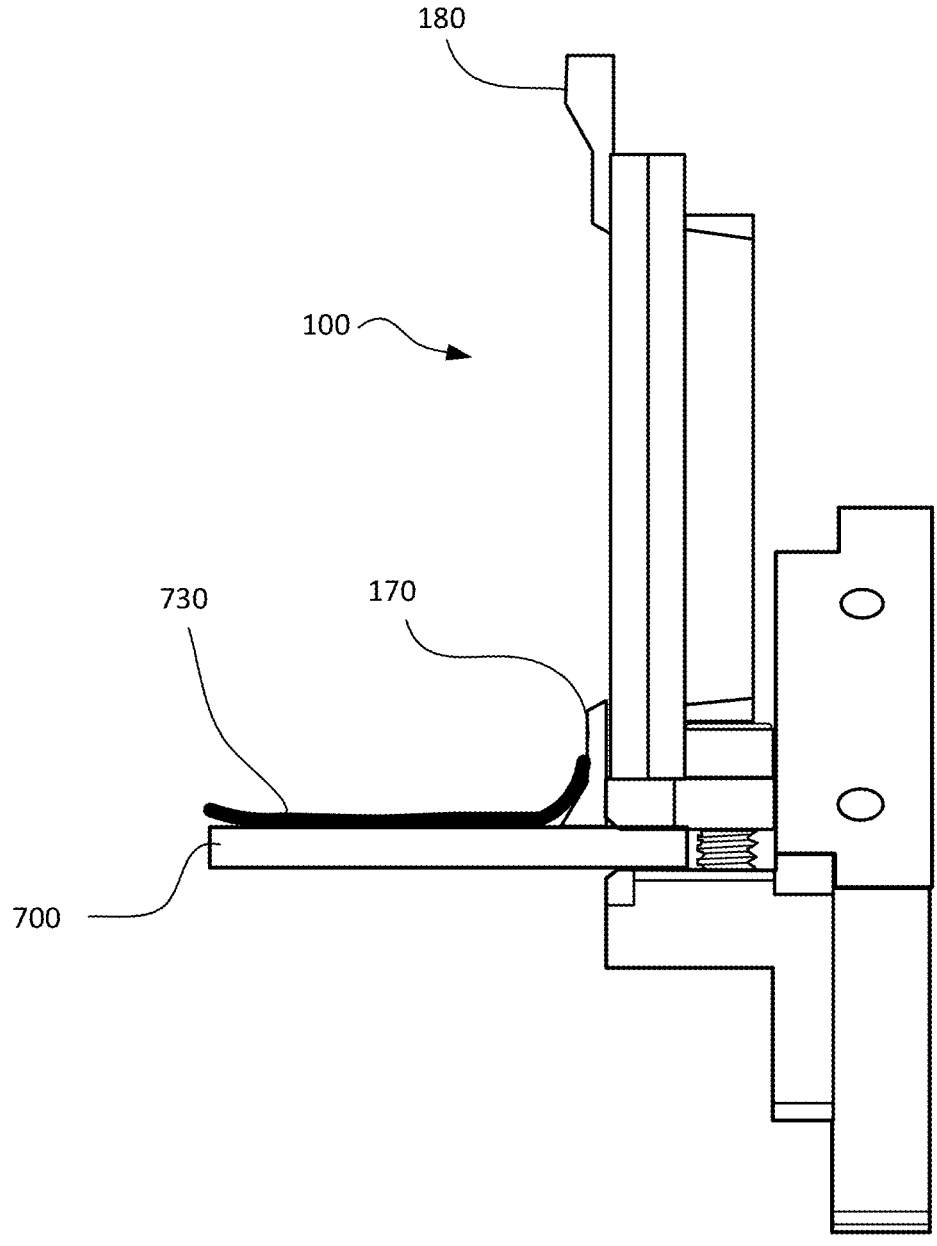
Figure 7D:
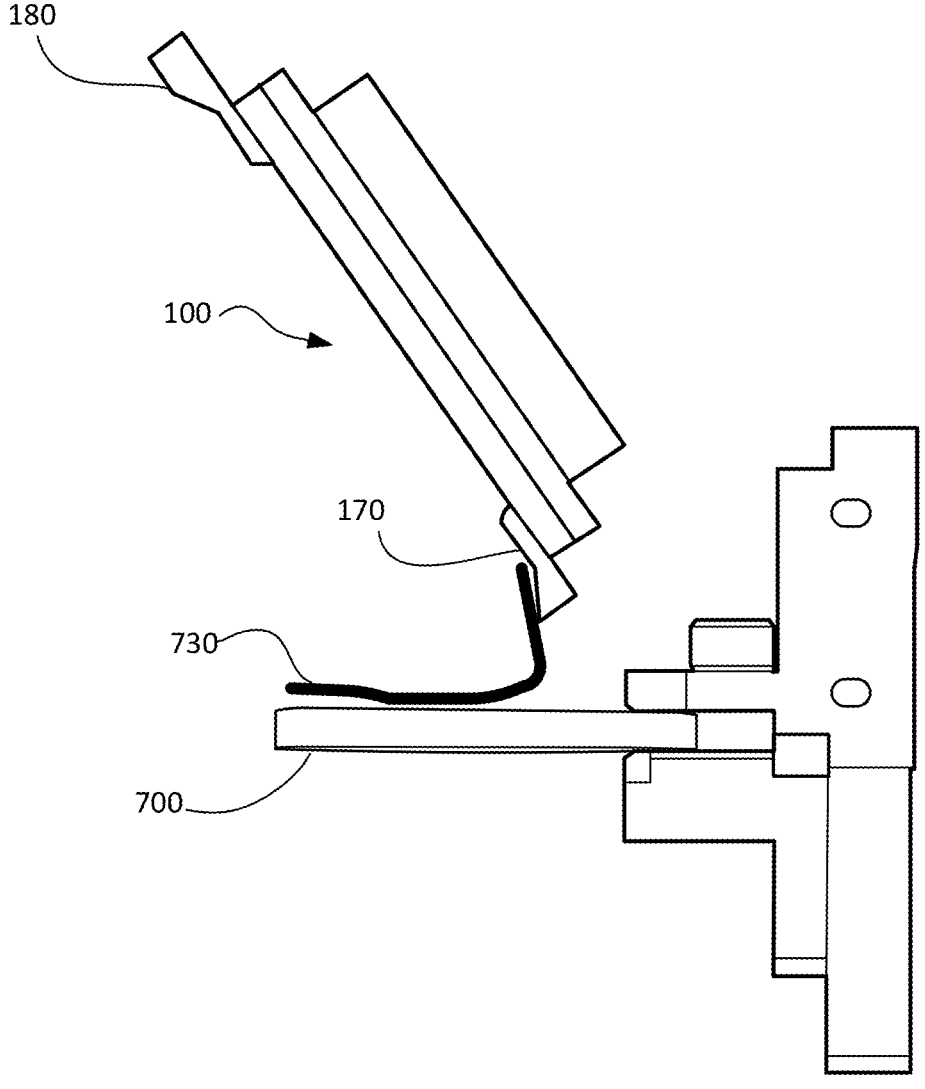

FIG. 7B shows the apparatus 100 of FIG. 6 attached to the flat optic 700. As described above, the first leg 170 may be shorter than the second leg 180. The length of the first leg 170 may facilitate uniform and flush contact with the flat optics. In some embodiments, an adhesive solution (e.g., a polymer solution) can be applied to the exterior surface of the first leg 170. For example, a polymer solution can be applied to the exterior surface of the first leg 170 and then applied onto flat optics 700 to bond the first leg 170 to the flat optics. FIG. 7C shows a polymer solution applied to the flat optics 700 and a portion of the first leg 170 to form a polymer film 730. The polymer film 730 can contact the flat optics 700 and the portion of the first leg 170 for a sufficient period of time for the polymer solution to transition to the polymer film 730. FIG. 7C shows the apparatus 100 being removed from the flat optics 700 to peel the polymer film 730 from the flat optics 700. Specifically, the second leg 180 can be manipulated to begin peeling the polymer film 730 from the flat optics 700. The first leg 170 facilitates peeling of the polymer film 730 from the surface of the flat optics 700 without the use of any external tools that may damage the optics.

In some embodiments, a kit is provided. The kit may include a lens, a polymer film, and any of the apparatuses discussed herein. The kit may include an apparatus as shown in FIG. 7A that can be attached to a lens surface via the polymer film. For example, the polymer film can be applied to the lens surface and the apparatus as described in FIGS. 7A-7D. In this embodiment, the apparatus and the dried polymer film are situated in place on the lens surface when shipping a lens or a camera including a lens. The end user peels the polymer film from the lens surface before use of the lens. The kit provides protection to a lens during shipping. For example, the raised nature of the apparatus prevents any objects or debris from contacting the lens surface. Additionally, the end user can peel the polymer film from the lens when ready for use.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A method of cleaning a lens of an eye-imaging device, the method comprising:
   providing an eye-imaging device comprising a tip including a lens;
   providing an apparatus for receiving a cleaning solution, wherein the apparatus comprises:
      an annular base comprising an orifice, the annular base comprising a first end and a second end;
      a contact member disposed adjacent to the second end of the annular base, wherein the contact member has a diameter less than the annular base such that the contact member fits within the annular base, wherein the contact member includes a contact surface; and
      a top region disposed at the first end of the annular base, the top region comprising a lip extending outwardly away from the annular base;
      wherein the contact surface includes a first contact end and a second contact end, wherein the contact surface tapers from the first contact end to the second contact end; and
   attaching the apparatus to the tip of the eye-imaging device;
   filling the apparatus with the cleaning solution;
   contacting the cleaning solution with the lens for a period of time to allow the cleaning solution to dry to form a film;
   entrapping dirt and debris from the lens into the film; and
   cleaning the lens by removing the film from the lens of the eye-imaging device.

2. The method of claim 1, wherein attaching the apparatus to the eye-imaging device comprises press fitting the apparatus to the eye-imaging device such that the contact surface of the contact member is flush with the tip of the eye-imaging device.

3. The method of claim 1, further comprising removing the apparatus from the eye-imaging device.

4. The method of claim 3, wherein the cleaning solution comprises a polymer solution comprising a solvent and a polymer.

5. The method of claim 4, wherein the method further comprises contacting the polymer solution with the lens for a period of time for the solvent to dry to form a polymer film.

6. The method of claim 4, wherein the method further comprises sealing the top region of the apparatus to prevent leakage of the cleaning solution.

* * * * *